(12) United States Patent
Sealfon

(10) Patent No.: US 10,556,100 B2
(45) Date of Patent: Feb. 11, 2020

(54) CONNECTOR WITH FILTER

(71) Applicant: REPRO-MED SYSTEMS, INC., Chester, NY (US)

(72) Inventor: Andrew I Sealfon, Monroe, NY (US)

(73) Assignee: Repro-Med Systems, Inc., Chester, NY (US)

(*) Notice: Subject to any disclaimer, the term of this patent is extended or adjusted under 35 U.S.C. 154(b) by 666 days.

(21) Appl. No.: 15/112,943

(22) PCT Filed: Feb. 20, 2015

(86) PCT No.: PCT/US2015/016929
§ 371 (c)(1),
(2) Date: Jul. 20, 2016

(87) PCT Pub. No.: WO2015/127285
PCT Pub. Date: Aug. 27, 2015

(65) Prior Publication Data
US 2016/0339226 A1      Nov. 24, 2016

Related U.S. Application Data

(60) Provisional application No. 61/942,488, filed on Feb. 20, 2014.

(51) Int. Cl.
*A61M 39/12* (2006.01)
*A61M 39/20* (2006.01)
(Continued)

(52) U.S. Cl.
CPC ............ *A61M 39/12* (2013.01); *A61M 5/165* (2013.01); *A61M 39/10* (2013.01);
(Continued)

(58) Field of Classification Search
CPC .. A61M 39/12; A61M 5/165; A61M 39/1011; A61M 39/10; A61M 2039/1066;
(Continued)

(56) References Cited

U.S. PATENT DOCUMENTS 3,386,585 A    6/1968   Weyand et al.
3,631,654 A *  1/1972   Riely .................... A61M 5/165
                                                210/446
(Continued)

FOREIGN PATENT DOCUMENTS

EP         0887085       12/1998
GB         2383828        7/2003
WO    WO2007/008511       1/2007

OTHER PUBLICATIONS

EPO Search Report for EPO Application 15752776.3 search report data dated Oct. 6, 2017 (Oct. 6, 2017).
(Continued)

*Primary Examiner* — Nathan R Price
*Assistant Examiner* — Melissa A Snyder
(74) *Attorney, Agent, or Firm* — Daniel W. Roberts; Law Offices of Daniel W. Roberts, LLC

(57) ABSTRACT

The present disclosure relates to a connector for connecting flow channels, flow regulators and/or reservoirs for directing flow. In some embodiments, the connector is a medical connector for connecting fluid flow controlling elements used in medical applications, particularly in infusion systems, such as tubes, syringes, needles, catheters and fluid reservoirs. The connector reduces the risk of contamination during handling and enhances safety when administering therapeutic solutions into a patient.

50 Claims, 11 Drawing Sheets

(51) Int. Cl.
*A61M 39/10* (2006.01)
*A61M 5/165* (2006.01)

(52) U.S. Cl.
CPC ........ *A61M 39/1011* (2013.01); *A61M 39/20* (2013.01); *A61M 2039/1033* (2013.01); *A61M 2039/1077* (2013.01); *A61M 2205/7509* (2013.01); *A61M 2205/7518* (2013.01); *A61M 2205/7545* (2013.01)

(58) Field of Classification Search
CPC .. A61M 2039/1033; A61M 2039/1077; A61M 5/12
See application file for complete search history.

(56) References Cited

U.S. PATENT DOCUMENTS

| | | | |
|---|---|---|---|
| 3,815,754 A | 6/1974 | Rosenberg | |
| 5,603,792 A * | 2/1997 | Guala | A61M 1/3639 156/245 |
| 5,630,792 A | 2/1997 | Guala et al. | |
| 5,731,227 A | 4/1998 | Sealfon | |
| 7,497,484 B2 * | 3/2009 | Ziman | A61M 39/10 285/396 |
| 2004/0238776 A1 * | 12/2004 | Peters | A61M 5/347 251/149.1 |
| 2005/0132826 A1 * | 6/2005 | Teugels | A61M 1/3639 73/866.5 |
| 2008/0183155 A1 | 7/2008 | Funamura et al. | |

OTHER PUBLICATIONS

PCT International Search Report for International Application PCT/US2015/016929, search report data of mailing May 15, 2015 (May 14, 2015).

* cited by examiner

CONNECTOR WITH FILTER

1. CROSS REFERENCE TO RELATED APPLICATIONS

This application claims the benefit under 35 U.S.C. § 119(e) of U.S. Provisional Application No. 61/942,488 filed Feb. 20, 2014, the entire contents of which is incorporated herein by reference.

2. BACKGROUND

Various types of infusion systems connect combinations of tubes, flow controllers, syringes, fluid reservoirs, pumps, and injection needles. Handling and connecting the different elements and operating the infusion system have the potential for introducing contaminants during administration. For example, when a user handles a connector to connect it to another element of the infusion set up, such as another tube, syringe, catheter, pump and fluid reservoir, the user may inadvertently make contact with a portion of the connector that comes into contact with the fluid to be delivered, thus contaminating the fluid.

In addition, infusion solutions can contain particulates, such as glass particles from opening glass ampoules, particles generated from needles piercing rubber septums, and particulates present in drug formulations. Some particulates are generated by freezing-thawing of drug solutions while some may be the result of incomplete dissolution of drugs in solution reconstituted before infusion. Entry of particles into the body, particularly the circulatory system, by infusion can lead to potential health complications, including, among others, inflammation, sepsis, and thrombosis.

In view of the foregoing, desirable are devices for use in infusion systems that increase safety and reduce the risk of health complications from administering therapeutic fluids by infusion.

3. SUMMARY

Provided in one aspect is a medical connector comprising a body defining a first opening at a distal end, a second opening at a proximal end, and a passageway connecting the first and second openings; a connector at the distal end; a proximal region toward the proximal end of the body configured for holding the medical connector; a flange protruding from the body between the proximal region and the connector; and a filter interposed in the passageway between the first opening at the distal end and the second opening at the proximal end. The passageway provides a fluid flow path between the first opening and second opening. The flange is dimensioned to shield the connector at the distal end from contamination when handling the medical connector at the proximal region and, in certain embodiments, brace the medical connector when force is applied on it. The filter positioned in the passageway removes particulates that may be present in the fluid flowing through the passageway. In certain embodiments, the filter is selected from a coarse filter, microporous filter, an ultrafiltration membrane, or combinations thereof.

In certain embodiments, the medical connector further comprises a first cap or plug for covering the first opening at the distal end. A second cap or plug for covering the second opening at the proximal end can also be present.

In certain embodiments, the medical connector further comprises a tubing, particularly a flexible tubing, attached to the proximal end. In some embodiments, the tubing at the end not attached to the proximal end can be attached to another connector, or in certain embodiments, attached to an injection needle, such as for subcutaneous or intravenous administration.

In another aspect, provided is an infusion system comprising the medical connector for infusion of therapeutic fluids into a patient. The medical connector of the infusion system can have a flexible tubing attached at the proximal end, where the tubing at the end not attached to the proximal end is attached to an injection needle or another connector. The infusion system can further comprise a pump, particularly a constant force syringe spring pump.

In a further aspect, provided is a kit comprising the medical connector of the present disclosure. In some embodiments, the kit further comprises a tubing set. In certain embodiments of the kit, a flexible tubing is attached to the proximal end of the medical connector. In certain embodiments, the kit also comprises an injection needle set, such as for subcutaneous or intravenous administration of therapeutic solutions. The needle can be separate or where the kit further comprises a tubing, the needle can be attached to the end of the tubing not connected to the medical connector. In additional embodiments, the kit comprising the medical connector further includes a pump, particularly a constant force syringe spring pump.

4. BRIEF DESCRIPTION OF THE FIGURES

Figure 1:
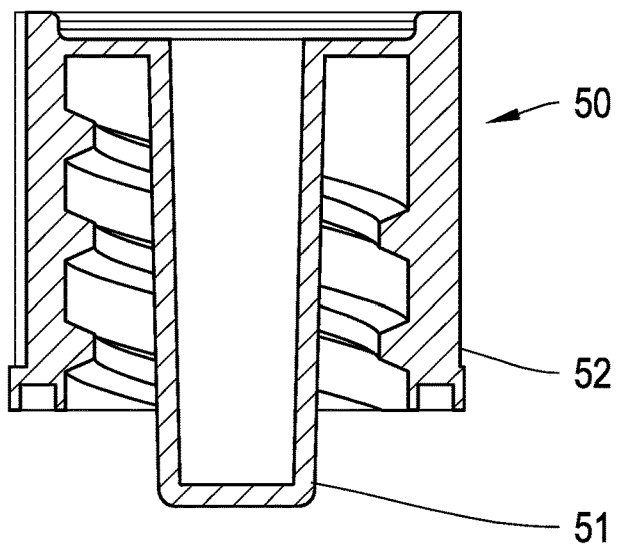
FIG. 1 is a cross sectional view of an embodiment of the medical connector, and a cap for covering the distal end of the connector.
Figure 1:
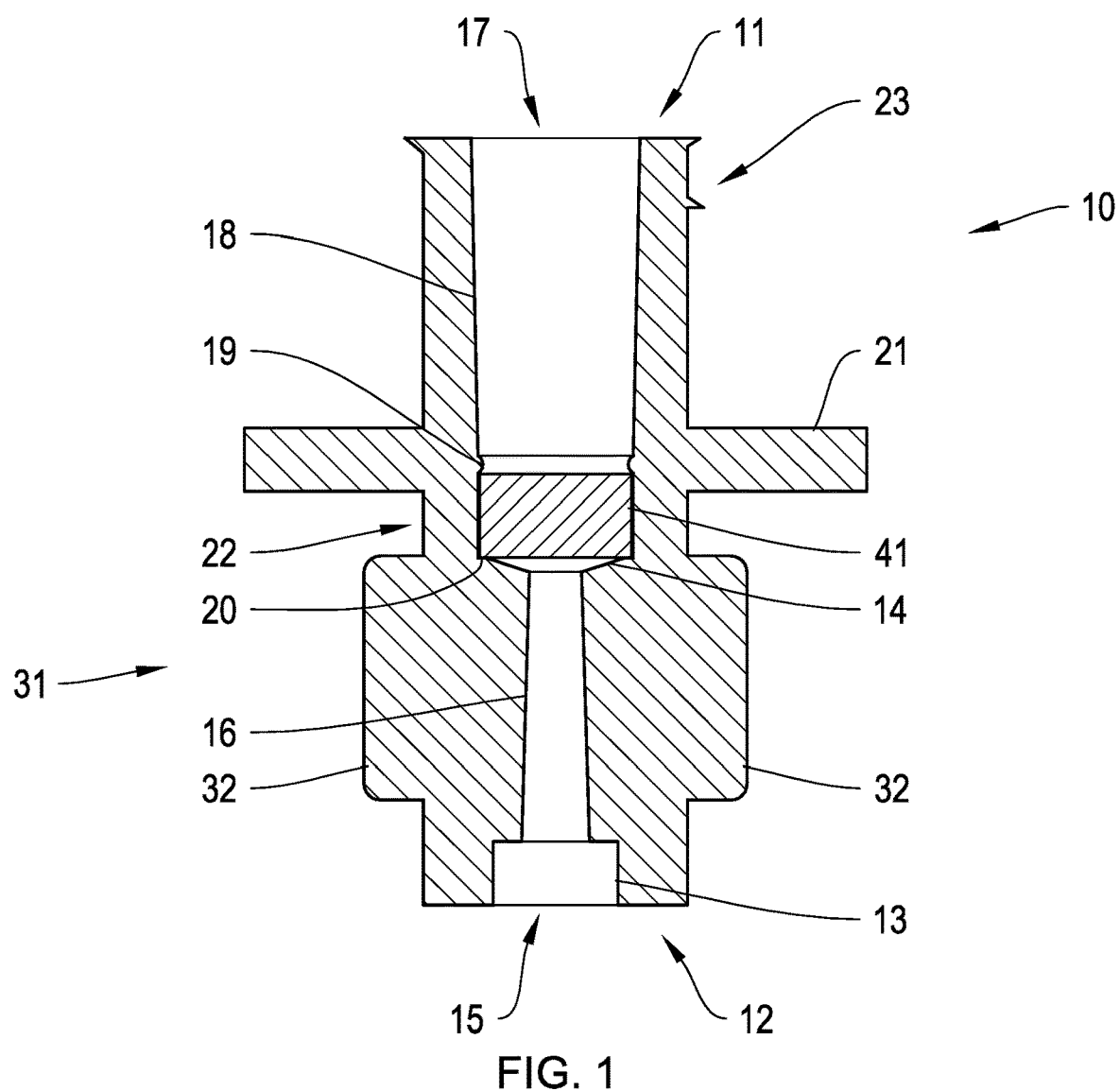
Figure 2:
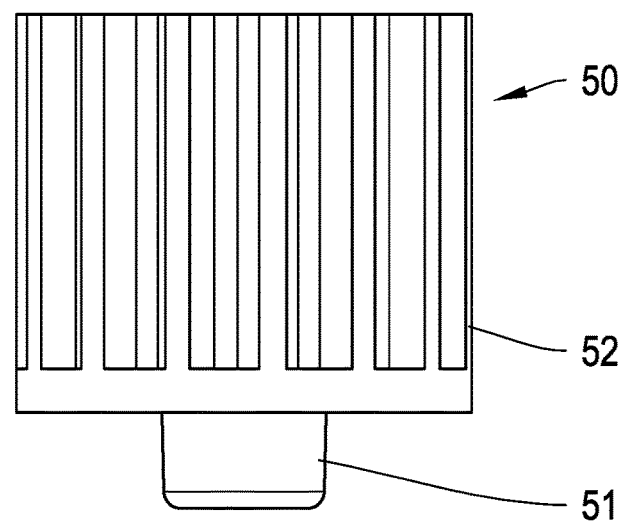
FIG. 2 is a side elevational view of the medical connector and the cap of FIG. 1, with the body positioned to show the top of a fin on the proximal region of the body.
Figure 2:
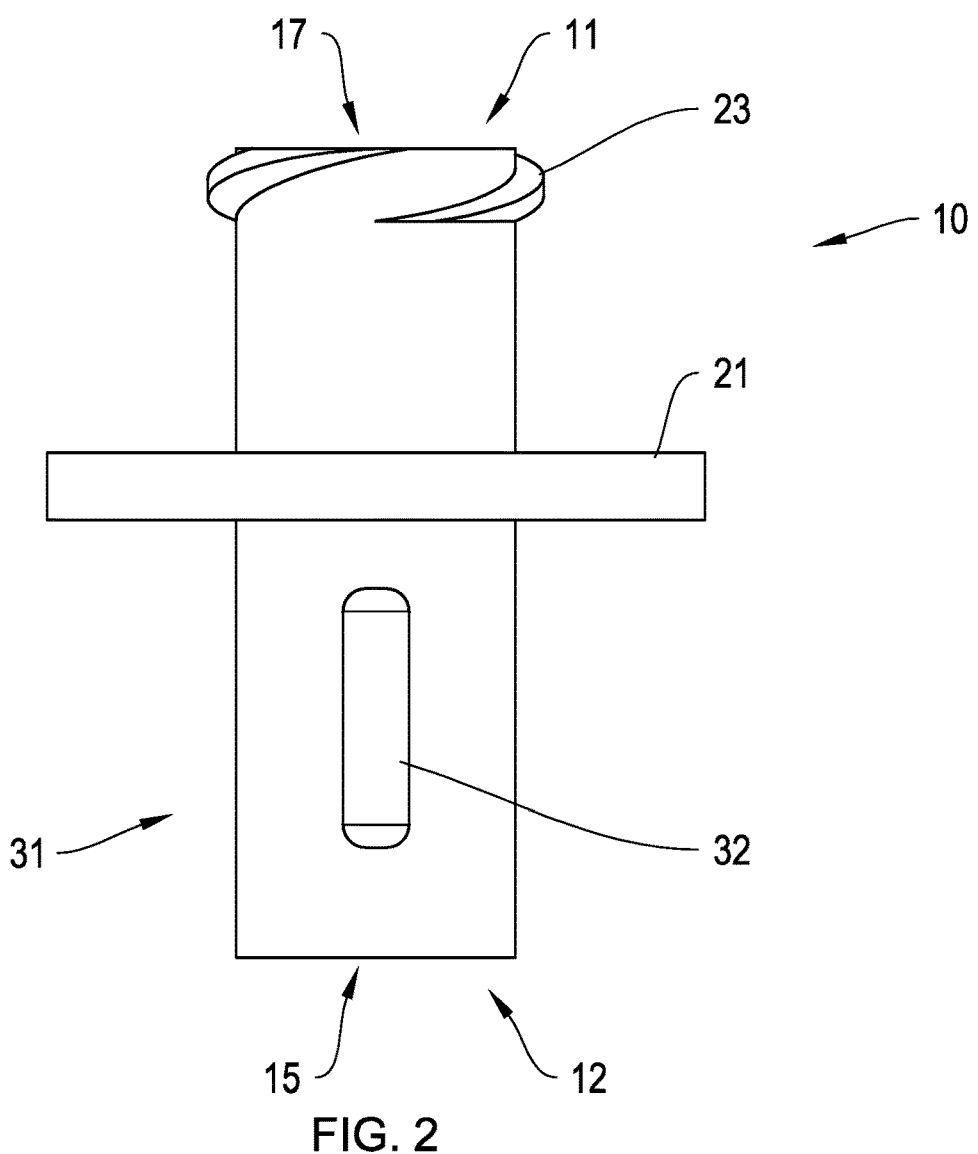
Figure 3:
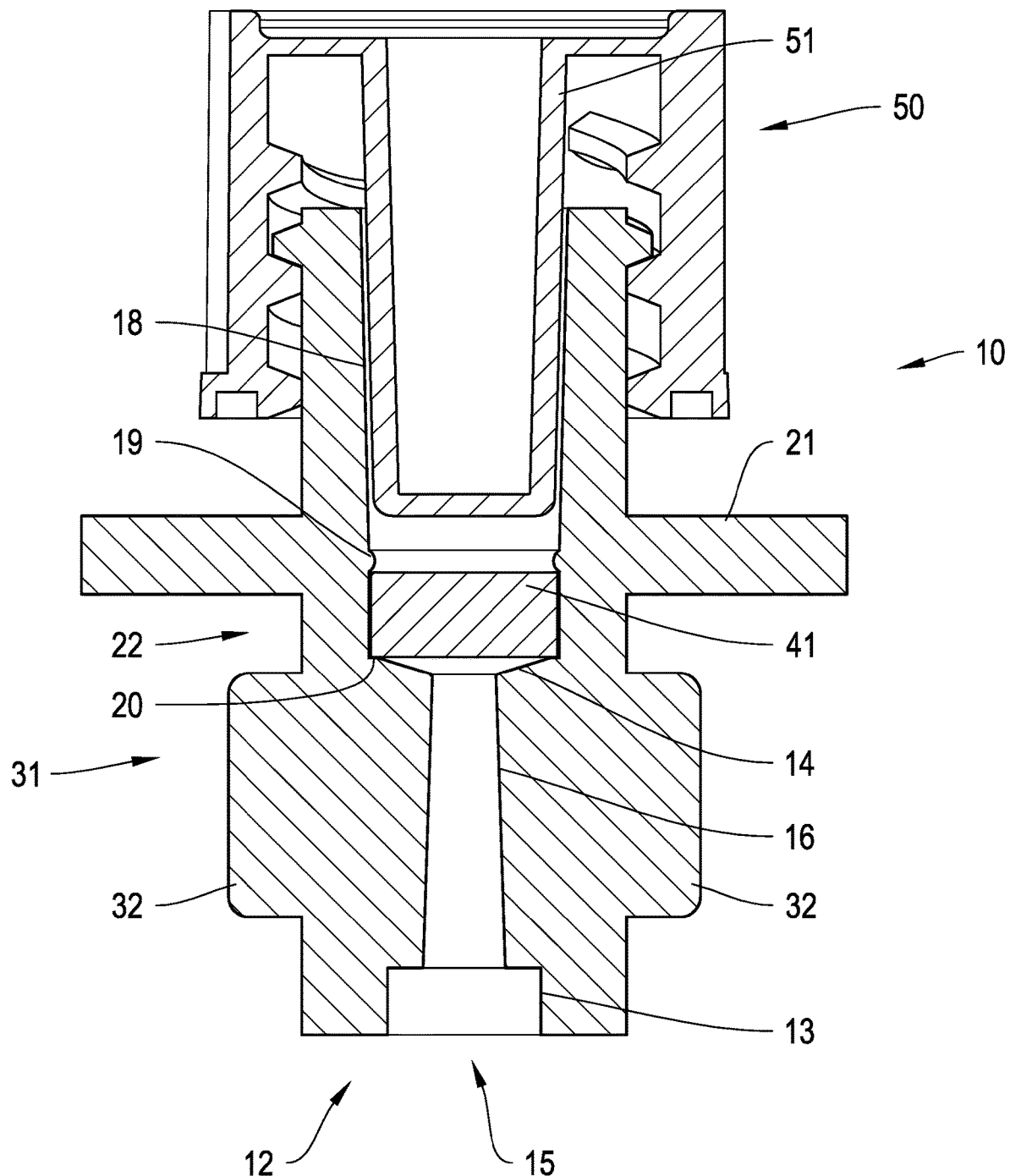
FIG. 3 is a cross-sectional view of the medical connector of FIG. 1 with the cap engaged on the corresponding luer connector at the distal end of the medical connector.
Figure 4:
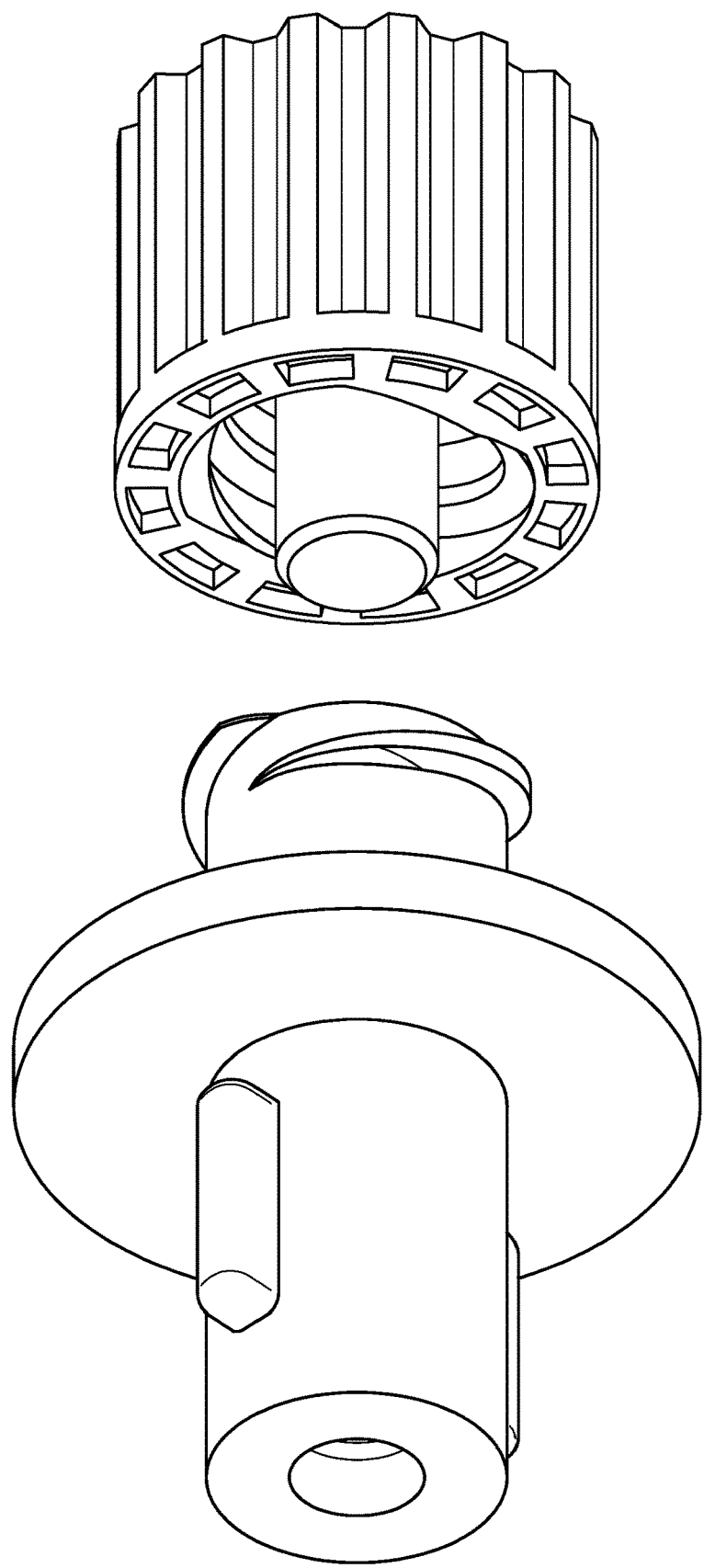
FIG. 4 is a perspective view from below the proximal end of the medical connector and the cap of FIG. 1.
Figure 5:
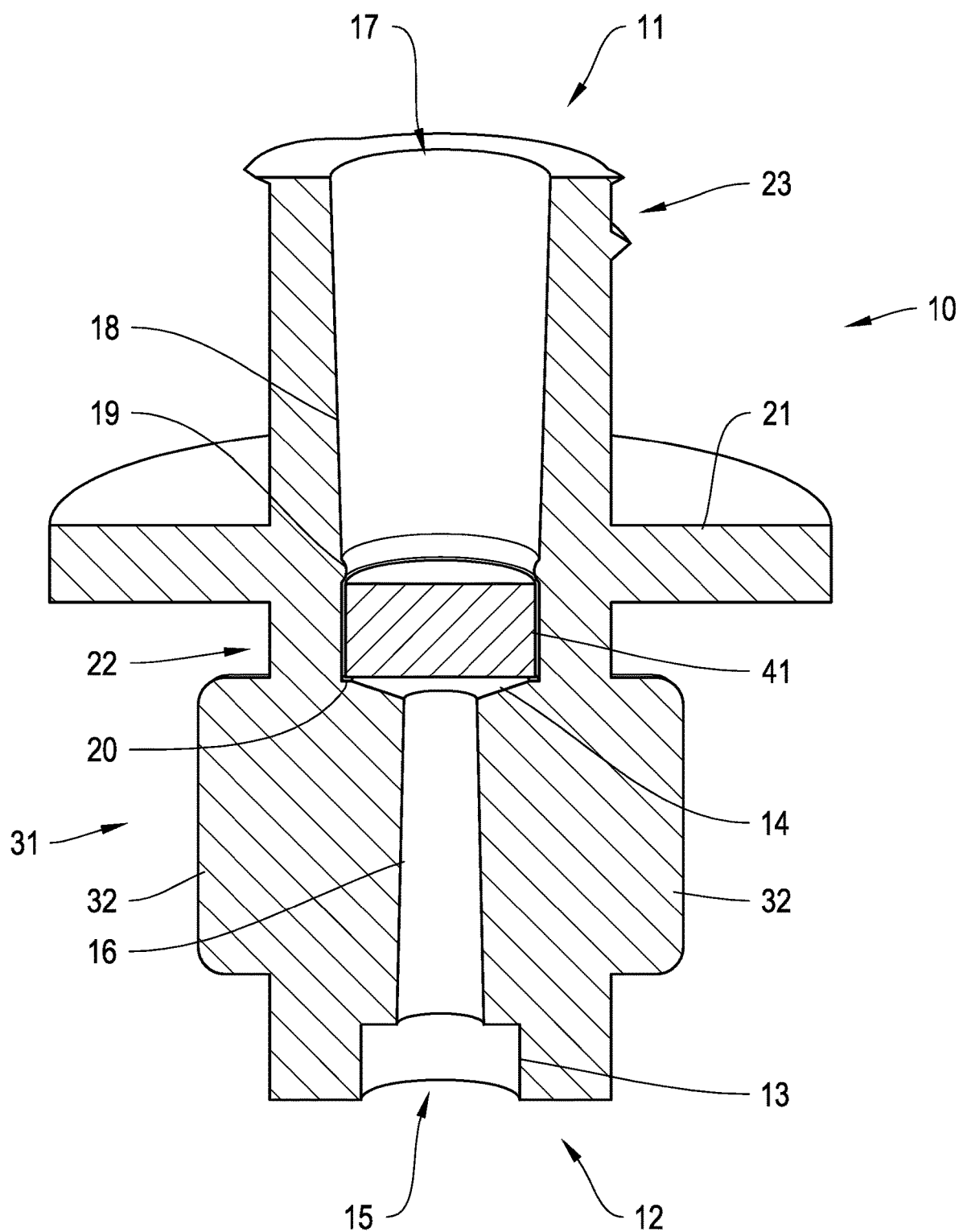
FIG. 5 is a cross-sectional perspective view of the medical connector of FIG. 1 without the cap.
Figure 6:
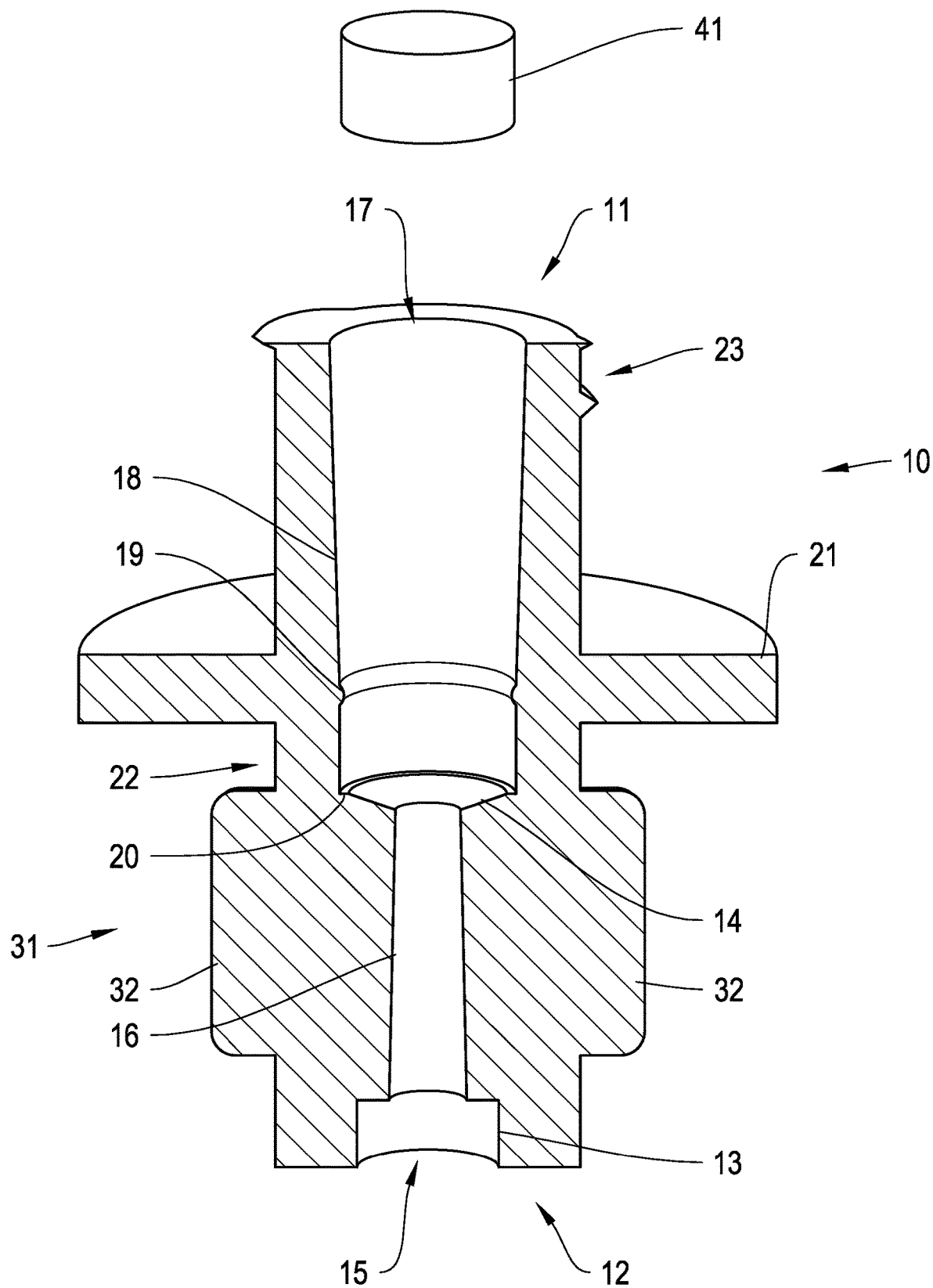
FIG. 6 is a cross-sectional perspective view of the medical connector of FIG. 5 with the filter removed for viewing of the passageway.
Figure 7:
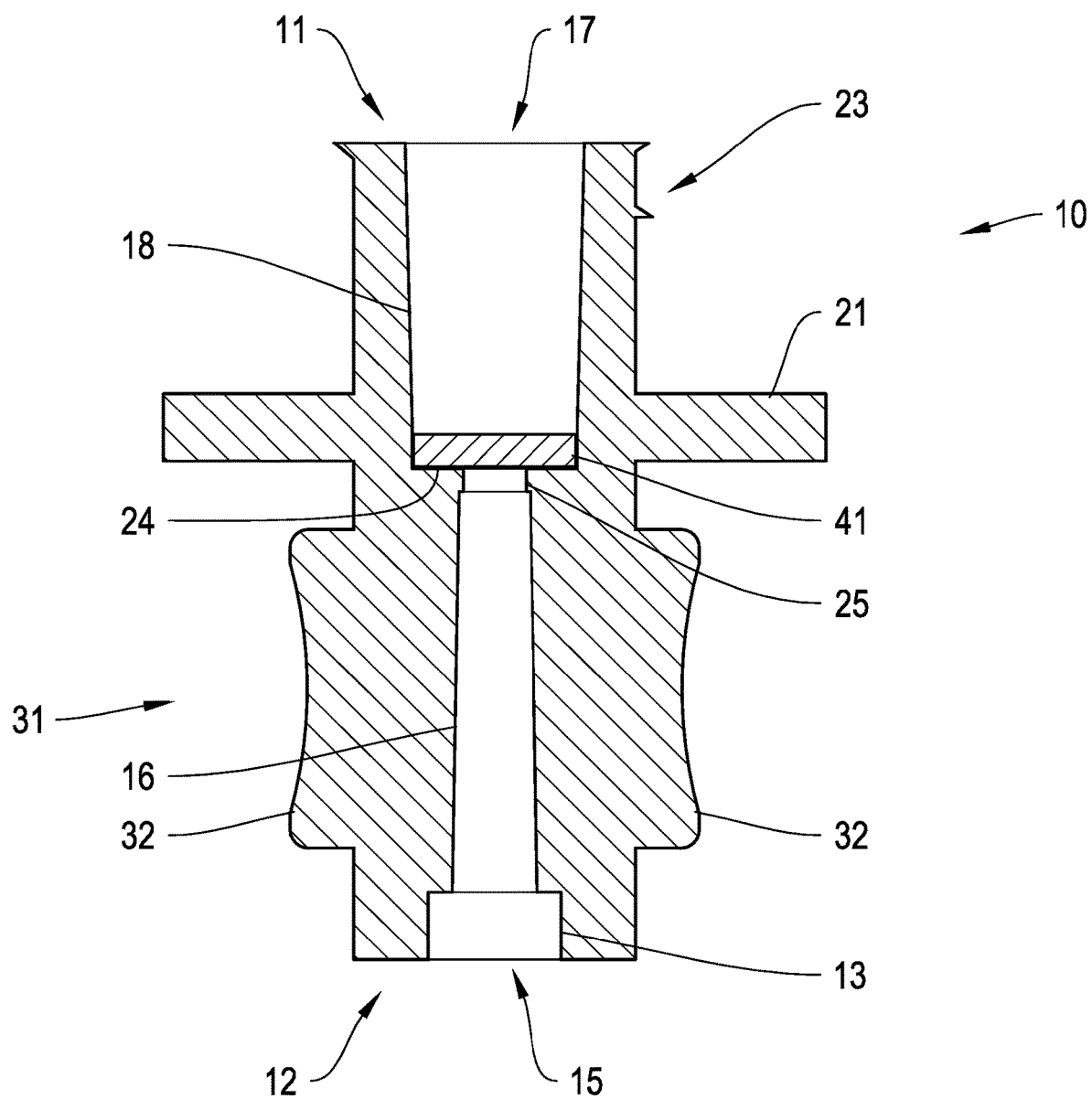
FIG. 7 is a cross-sectional view of another embodiment of the medical connector, where the fins have recessed upper portions.
Figure 8:
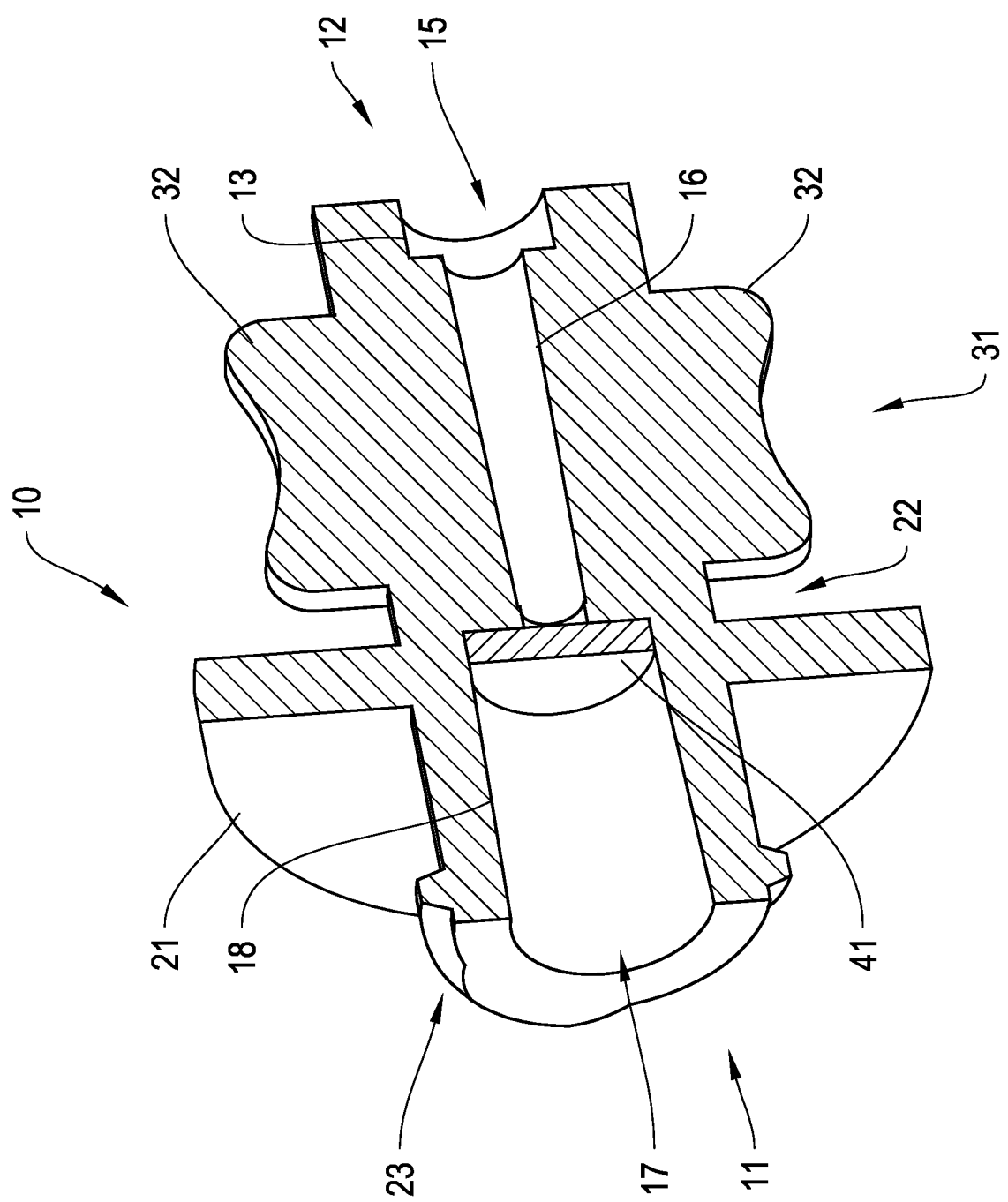
FIG. 8 is a cross-sectional perspective view of the medical connector of FIG. 7.
Figure 9:
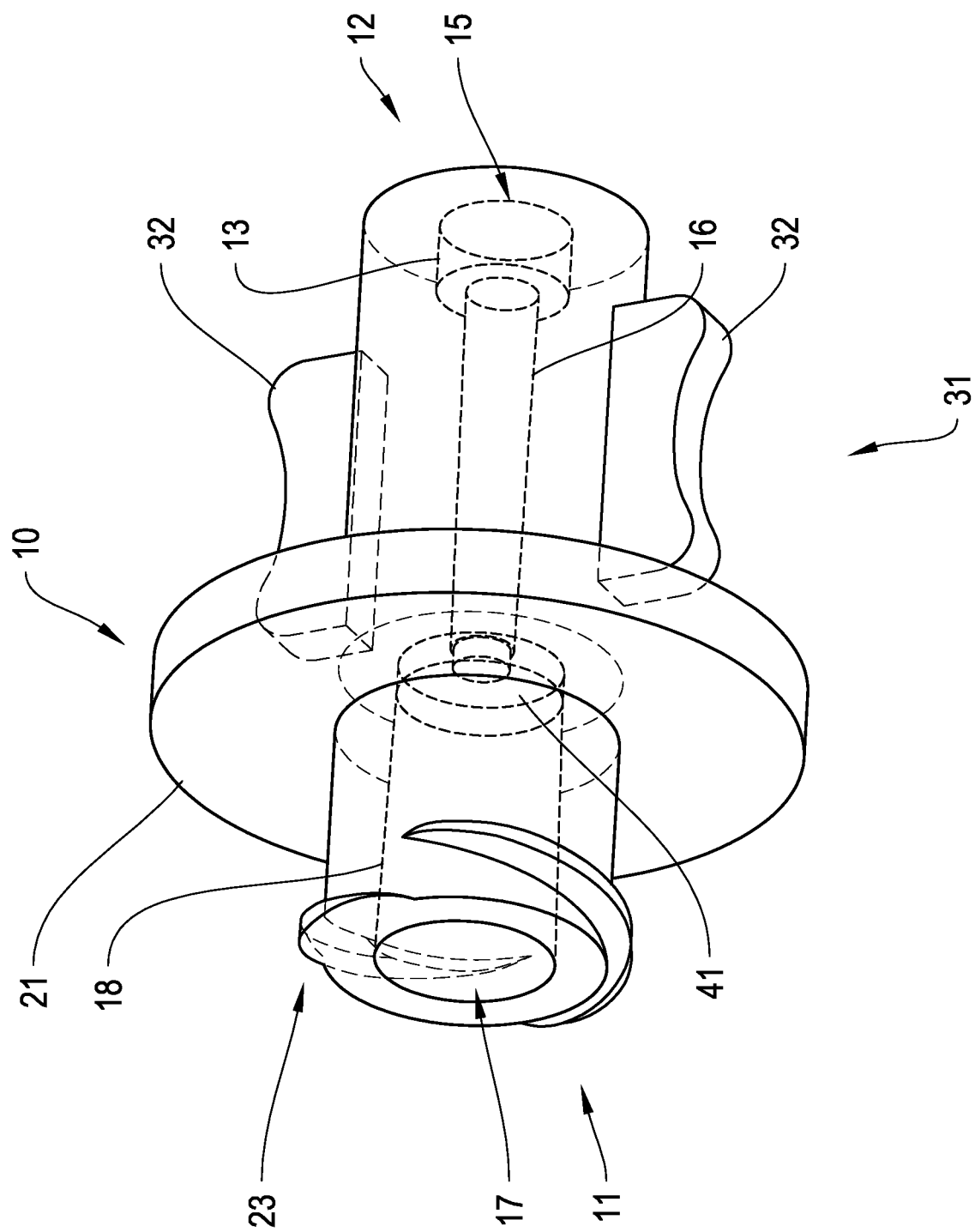
FIG. 9 is a phantom perspective view of the medical connector of FIG. 7.
Figure 10:
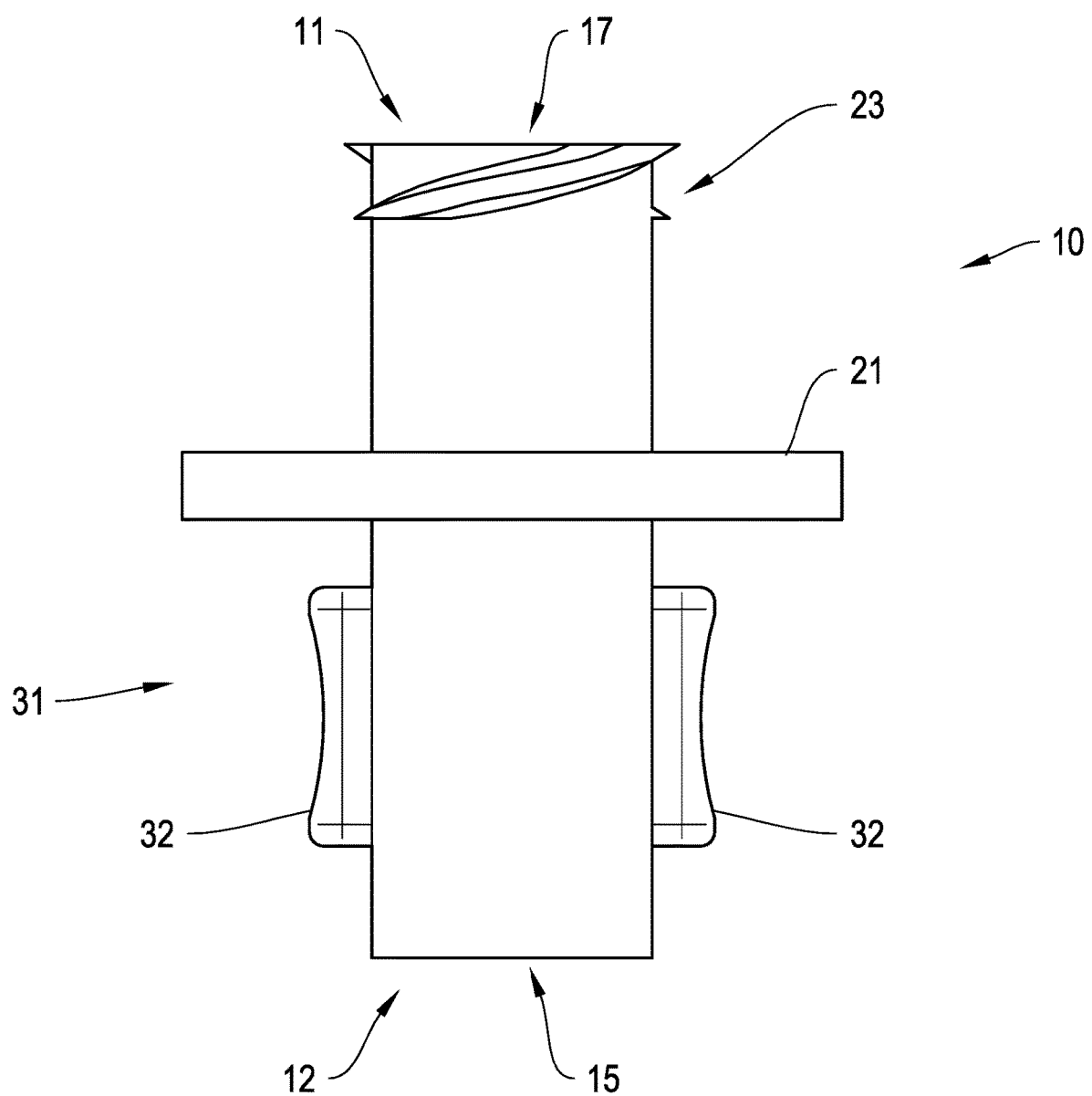
Figure 11:
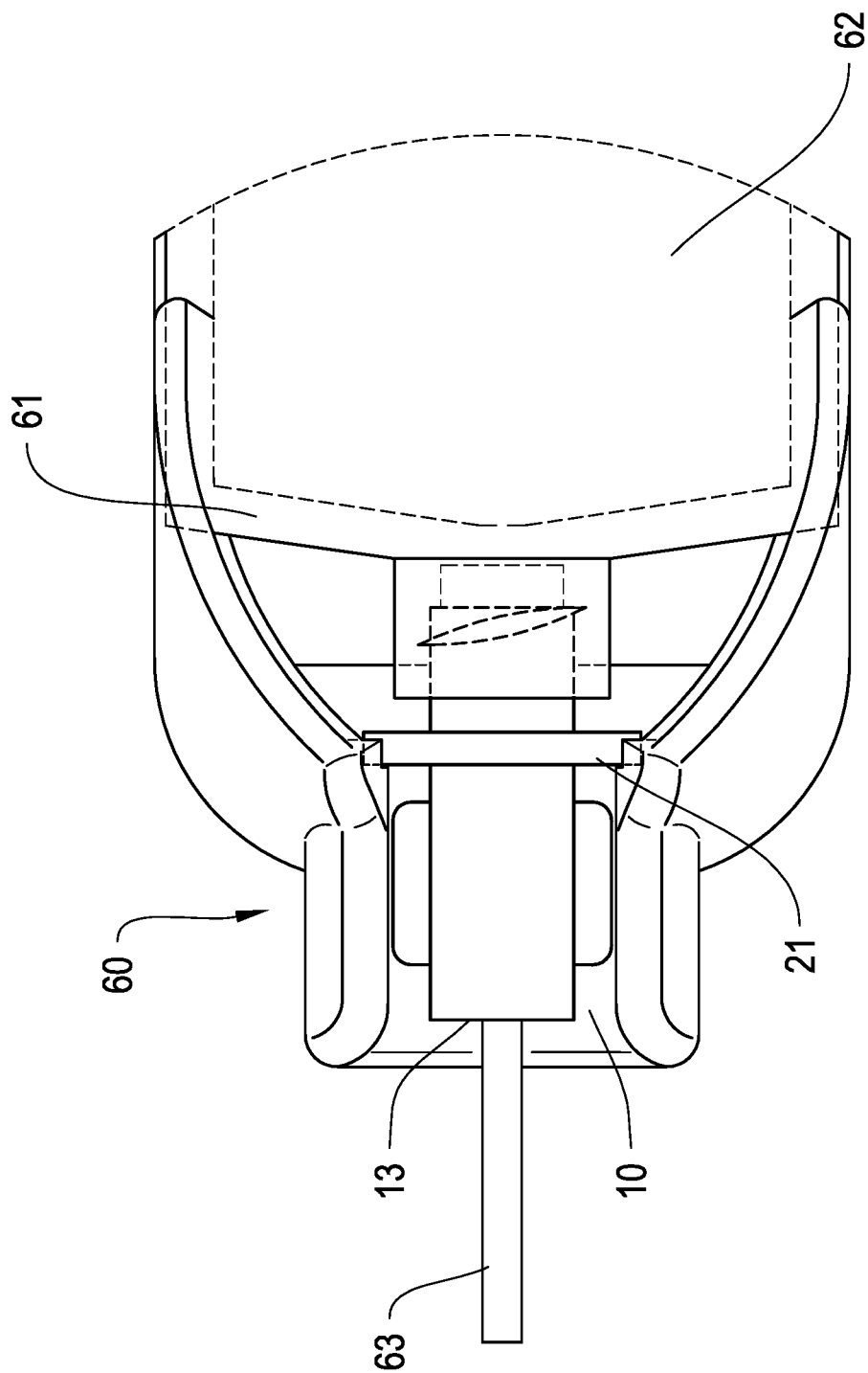

FIG. 10 is a side elevational view of the medical connector of FIG. 7, with the body positioned to show the side of the fins with the recessed upper portions; and FIG. 11 shows an embodiment of a medical connector of the disclosure having a flexible tubing attached to the proximal section of the passageway, where the medical connector is attached to an outlet of a syringe and held in an open collar with the flange resting against the side of the collar facing the syringe.

5. DETAILED DESCRIPTION

Setting up an infusion system for administration of a therapeutic fluid involves connecting, among others, various combinations of tubings, flow regulators, syringes, pumps, fluid reservoirs and injection needles. Various types of infusion setups are described in, among others, U.S. Pat. Nos. 8,162,876; 7,303,543; 5,741,227; and 4,569,675. Assembling the infusion system can lead to contamination during handling. Moreover, the therapeutic solution for administration can contain particulates, which upon entering the body can cause adverse health events, such as inflammation, sepsis, and thrombosis. Accordingly, the present disclosure provides a connector with features that reduce the risk of contamination during handling/assembly, increase convenience of use, and provide additional safety in administering therapeutic fluids. While the connector can be adapted for gas and liquid applications, in preferred embodiments, the connector is useful in medical applications for fluid transport, such as in connecting parts of an infusion system. In certain embodiments, the medical connector is used with a syringe, such as a syringe pump, and connects the syringe to a tubing member and/or an injection needle member.

In the following detailed description, the singular forms "a", "an" and "the" include plural referents unless the context clearly indicates otherwise. Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

In one aspect, the medical connector comprises a body defining a first opening at a distal end, a second opening at a proximal end, and a passageway, such as a channel, connecting the first opening and the second opening, a connector at the distal end, a proximal region on the body, a flange protruding from the body between the proximal region and the connector at the distal end, and a filter interposed in the passageway between the first opening and the second opening.

In certain embodiments, the body comprises a substantially cylindrical body defining a first opening at the distal end, a second opening at the proximal end, and a passageway connecting the first opening and the second opening.

The first opening at the distal end and the second opening at the proximal end can be of different shapes and/or dimensions, for example to accommodate connecting to other members, such as tubes, syringes, flow regulators, fluid reservoirs and catheters. In certain embodiments, the first opening at the distal end and the second opening at the proximal end can be a substantially circular opening, such as defined by the geometry of the passageway and/or connector.

The passageway provides a fluid flow path between the first opening at the distal end and the second opening at the proximal end. In preferred embodiments, the passageway is a centrally located passageway, extending along the longitudinal axis of the body. In certain embodiments, the passageway is of uniform dimension (e.g., diameter) throughout the fluid path, from the first opening at the distal end to the second opening at the proximal end. In certain embodiments, the passageway can comprise different configurations or dimensions, particularly different bore sizes (e.g., passageway diameter), such as to accommodate various features of the medical connector. In certain embodiments, the passageway comprises a distal section and an inner section, e.g., an inner passageway, where the distal section and the inner section have different bore sizes, for example, bore sizes of different diameters, such as to accommodate a filter, affect fluid flow, and/or function as a connector. In various embodiments, the cross-sectional area of the distal section is different from the cross-sectional area of the inner section of the passageway. In various embodiments, the bore size of the distal section is larger than the bore size of the inner section of the passageway. In certain embodiments, the distal section of the passageway is configured to act as a connector, as further described herein. The distal section of the passageway can be uniform (e.g., cylindrical), or be inwardly tapered (e.g., frustoconical) along the longitudinal axis towards the proximal end, such as to accommodate another connector member. In a preferred embodiment, the distal section of the passageway is inwardly tapered to connect to a male luer connector, particularly a male luer lock. In certain embodiments, the interface between the distal section and the inner section of the passageway forms an annular surface. In such embodiments, the radial distance from the inside edge to the outer edge of the annular surface is defined by the bore size (e.g., diameter) of the distal section of the passageway and the bore size (e.g., diameter) of the inner section of the passageway at the interface. In certain embodiments, the annular surface at the interface is a flat annular surface. Where the bore size of the distal section is larger than the bore size of the inner section of the passageway, the exposed flat annular surface faces the distal end of the medical connector. In some embodiments, the annular surface at the interface is a non-flat annular surface. In certain embodiments, where the bore size of the distal section is larger than the bore size of the inner section of the passageway, the annular surface at the interface is tapered inward towards the proximal end, such as to form a frustrum, e.g., frustroconical, to the inner section of the passageway. The frustroconical interface can provide for optimal filtration by the filter. In certain embodiments, where the annular surface at the interface is tapered inward, a flat annular surface can be present at the outer edge of the frustrum in the distal section of the passageway, for example for holding a filter element or a support structure (e.g., foam, mesh, or weave) for supporting the filter in the passageway.

In certain embodiments, the inner section of the passageway can be uniform or tapered along the longitudinal axis of the passageway. In certain embodiments, the inner section of the passageway along the longitudinal axis towards the proximal end is tapered outward, such as to provide decreased resistance to fluid flow. In certain embodiments, the inner section can have a constriction for affecting flow resistance, such as at the end of the inner section of the passageway towards the distal end. In some embodiments, the proximal end of the inner section of the passageway can also be adapted or configured to act as a second connector, such as having an extended tube for connecting a tubing member or dimensioned as another luer connector, as further described below. In certain embodiments, the proximal section of the passageway is adapted to accept a tubing, for example by having a wider bore than the inner passageway for fitting the tubing.

The connector at the distal end of the body, and in some embodiments, the second connector at the proximal end of the body, can comprise any type of suitable connector for connecting to another member, such as another connector, tubing, syringe, fluid reservoir, catheter, or pump. In some embodiments, the connector can comprise an extended tube at the distal and/or proximal end, which can form a friction tight connection to another tube. The extended tube can have one or more external annular ridges for holding the inner part of the tube and forming a tight seal. In a preferred embodiment, the connector at the distal end of the body comprises a luer connector, particularly for accepting a male luer connector. In certain embodiments, the luer connector is a luer lock or variations thereof, such a barbed luers and latch luers (see, e.g., U.S. Pat. Nos. 7,347,458; 7,128,348; 6,673,059; 6,332,633; 6,217,560; U.S. Pat. No. 5,984,373; and 5,772,643; all of which are incorporated herein by reference). In some embodiments, the connector at the distal end defines part of the distal section of the passageway, for example when dimensioned to accept a male luer connector.

The body of the medical connector towards the proximal end comprises a proximal region. In various embodiments, the proximal region allows for gripping and holding of the medical connector, particularly for gripping with fingers. The proximal region can be configured in any form suitable for gripping and holding the medical connector. For example, the proximal region of the body can have a substantially circular, substantially triangular, or substantially elliptical cross-section and extend along the longitudinal axis of the proximal region. The surface of the proximal region can include features to enhance gripping and holding, including outwardly protruding ridges or bumps; grooves, indentations or dimples; or textured surfaces. In some embodiments, surface of the proximal region has an elastomeric material to aid in gripping and holding the medical connector. Exemplary elastomeric materials include, among others, natural rubber and synthetic polymers, such as polyisoprene, polybutadiene, butyl rubber, styrene-butadiene, nitrile rubber, and ethylene propylene diene. In some embodiments, the proximal region is configured for the user to hold the medical connector and provide leverage for connecting the distal section to another member, such as a tubing or syringe, particularly connecting to another member via a luer connector. In a preferred embodiment, the body at the proximal region can have one or more fins protruding from the body, where the fins can be of sufficient size and rigidity to provide sufficient torque when turning the medical connector to connect to another member. In certain embodiments, the proximal region comprises 2 fins, for example on opposite sides of the proximal region of the body. In some embodiments, the proximal region comprises 3 fins, for example 3 fins positioned equidistant from each other around the proximal region of the body. In other embodiments, the proximal region comprises 4 or more fins positioned around the proximal region of the body.

The fins have a length along the longitudinal axis of the body and can protrude outwardly away from the longitudinal axis of the body for varying distances. The fins can have various configurations, including, among others, substantially rectangular, substantially square, or substantially triangular. In other embodiments, the fins are substantially circular, substantially elliptical, substantially rhomboid, or fan shaped. The fins can have rounded corners and/or edges, and in certain embodiments, a recessed upper portion or else contoured to provide comfortable surfaces to allow the user's fingers to engage the fins and turn the medical connector. In some embodiments, the fins have a coating of elastomeric material to aid in gripping with the fingers. The fins can be attached to the flange, as described in more detail below, or in other embodiments, be separate or spaced apart from the flange. Where the fins are spaced apart from the flange, the flange and the fins can be sufficiently spaced apart to accommodate fitting a collar to hold the medical connector via the space between the flange and the fins. In some embodiments, while the fins can be dimensioned to provide sufficient torque for turning the medical connector, the fins can also be dimensioned so that the medical connector fits through a collar, with the proximal region comprising the one or more fins resting on the collar (see, e.g., FIG. 11).

The medical connector comprises a flange protruding from the body between the proximal region on the body and the connector at the distal end. In certain embodiments, the medical connector comprises a flange protruding from the body between the one or more fins and the connector at the distal end. The flange can act as a shield to reduce the risk of contaminating the connector at the distal end during handling of the medical connector, particularly by the user's fingers touching the connector during connecting the medical connector to other members of an infusion system. In various embodiments, the flange is also of sufficient size, thickness, resiliency and rigidity when the flange is used to hold or brace the medical connector against pressure applied to it. For example, the medical connector can be attached to the outlet of a syringe through a luer, for example on a syringe pump, and when applying pressure on the syringe barrel, the flange is held in a collar to brace against the force applied to the syringe barrel. The flange can be of various shapes, including among others, substantially rectangular, substantially square, substantially elliptical or disc shaped, and of sufficient size, thickness, and rigidity to provide a shield against touching of the distal connector and/or to brace the medical connector when force is applied to it. In a preferred embodiment, the flange comprises a disc provided between the proximal region, particularly between the one or more fins, and the connector at the distal end. The flange can protrude straight from the body or have a curved shape. Where the flange is curved, it can be concave or convex with respect to the distal end of the body. In certain embodiments, the flange is curved, i.e., concave, towards the distal end.

In the embodiments of the medical connector, a filter is interposed in the passageway. As such, the filter is an in-line filter, which acts to remove certain particular contaminants from the substance flowing through the medical connector. The filter can be placed in any position along the longitudinal axis of the passageway, between the first opening at the distal end and the second opening at the proximal end. In certain embodiments, the filter is positioned in the distal section of the passageway. In particular embodiments, the filter is positioned at the interface between the distal section and the inner section of the passageway. More particularly, where the bore size of the distal section is larger than the bore size of the inner section of the passageway, the filter is positioned above a frustrum shaped interface between the distal section and the inner section of the passageway, thereby providing effective use of the full surface area of the filter when a fluid flows from the first opening at the distal end to the second opening at the proximal end. In certain embodiments, the edge of the filter rests on an annular flat surface present at the outer edge of the frustrum in the distal section of the passageway. The filter can be attached in the passageway to provide a tight seal and direct fluid flow through the filter. In various embodiments, the filter can be held in place by thermal fitting, friction fitting, an adhesive, a rubber O-ring, or sandwiched between the flat portion of the annular surface at the interface and another annular ring, for example a plastic ring. In some embodiments, the filter is sandwiched between mesh, foam, weave or other like material, which can be positioned securely in the passageway. For example, the mesh or weave can have an annular ring of material, such as plastic or metal, at the edge of the mesh or weave, which provides rigidity and allow the sandwich to be secured in the passageway. In some embodiments, for example, where the filter has sufficient strength, depth and malleability, the filter is held in place by a protruding ridge around the passageway, particularly a protruding annular ridge, which prevents the filter from being dislodged when the filter is set in place. The ridge can be continuous, or be in the form of interspersed ridges, such as fingers or nubs, holding the filter in place. In some embodiments, the filter can sit on top of a foam, mesh, weave or like material, where the foam, mesh or weave rests above the frustrum, where fluid can flow through the foam, mesh, weave, or like material.

In certain embodiments, the passageway can have an additional filter arranged between the first opening at the distal end and the second opening at the proximal end. In some embodiments, one or more additional filters may be arranged between the first opening at the distal end and the second opening at the proximal end. The additional filters may be the same as filter as the first filter, or may include one or more different membranes and/or materials. In some embodiments, multiple filters can be stacked and held in place at the interface of the distal section and inner section of the passageway.

In the embodiments of the medical connector, the filter can be composed of various materials and have different porosities. The filter can be hydrophilic or hydrophobic. In some embodiments, the filter is a coarse filter or membrane. A coarse filter as used herein have a porosity range of >10 um and up to about 500 um or more. A coarse filter can be made of, among others, glass fiber, nylon, polypropylene, polyethylene, cellulose, or metal (e.g., wire mesh). Such filters can be made by compacting fibers (e.g., random sized or defined length), by weaving the material (e.g., filaments), or by stamping out material having the appropriate porosity, for example porous polyethylene or metal screens.

In some embodiments, the filter is a microporous filter or membrane. Microporous filters or membranes as used herein have a porosity range of about 10 um to about 0.1 um. In various embodiments, the microporous membrane can be made of one or more materials including acrylic co-polymer, cellulose acetate, nitrocellulose, nylon, polyethersulfone (PES), polypropylene, polysulfone, polytetrafluoroethylene (PTFE), and polyvinylidene fluoride (PVDF). In some embodiments, the filter comprises a ceramic filter, which can have pore sizes as small as 0.2 um.

In some embodiments, the filter is an ultrafiltration membrane. Generally, ultrafiltration membranes have a porosity range of about 0.1 um to about 0.001 um. Ultrafiltration membranes are used to remove high molecular-weight substances, colloidal materials, and organic and inorganic polymeric molecules but allowing passage of low molecular-weight organics and ions such as sodium, calcium, magnesium chloride, and sulfate. Ultrafiltration membranes can be made of one or more materials including, among others, polysulfone, polypropylene, cellulose acetate, and regenerated cellulose.

In some embodiments, the filter can have porosities of a combination of coarse filter, microporous filter, and/or ultrafiltration membrane. For example, cellulose acetate, polypropylene, PTFE, glass fiber, and polyethylene sulfone can be prepared having porosities with >1 um and up to about 100 um. Such filters can be used as prefilters for filtering medical solutions for administration in a subject.

In some embodiments, the filter can be an asymmetric membrane. Generally, asymmetric membranes have larger pores on the upstream side of the membrane, which can act as a prefilter, while the downstream side has an smaller porosity acting as an exclusion zone, i.e., absolute cut off layer. This is in contrast to traditional filter membrane materials which have comparable pore sizes on both the upstream and downstream sides of the membrane. The graded nature of asymmetric membranes results in a sidedness to the membrane, requiring proper positioning of the upstream side of the membrane for optimal performance. The asymmetric membranes can be made of one or more materials including, among others, polyethersulfone (PES), polysulfone, polyvinylidene fluoride (PVDF), and combinations thereof.

Exemplary filter media and the range of porosity characteristics that can be used in the medical connector are provided in Table 1.

TABLE 1

| Filter Media | Minimum Pore Size | Maximum Pore Size |
| --- | --- | --- |
| Cellulose Acetate Membrane | 0.2 | 1.2 |
| Charged Nylon Membrane | 0.05 | 1.2 |
| Depth Polypropylene Media | 0.2 | 20 |
| PTFE Hydrophobic Membrane | 0.1 | 10 |
| Glass fiber | 0.2 | 30 |
| PTFE Hydrophilic Membrane | 0.2 | 5 |
| Polypropylene Membrane | 0.1 | 0.2 |
| Nylon Membrane | 0.05 | 1.2 |
| Natural Glass Fiber | 0.5 | 5 |
| Nylon non-woven media | 1 | 40 |
| Nylon Screen | 7 | 300 |
| Polypropylene Media | 0.3 | 70 |
| Polypropylene Screen | 250 | 500 |
| PES Membrane | 0.05 | 1.2 |
| Polyester Screen | 5 | 73 |
| Polyethylene Membrane | 0.1 | 1 |
| PVDF Membrane | 0.1 | 0.6 |

Appropriate types of filters can be selected by the those of skill in the art for the desired result based on the needs of the application and different properties of the filter material. By way of example and not limitation, 0.2 µm filters can be used for crystalline solutions and 1.2-µm filters for lipid-containing solutions. Positively charged 0.2 µm filters can be used for filtering out particles, air, and microorganisms. As discussed herein, filter can comprise a combination of filters, including adjacently stacked filters, which can be different or the same.

In some embodiments, the filter chosen is made of material resistant to sterilization procedures and without loss of performance, such as sterilization by heat, gamma radiation, electron beam radiation, liquid chemical sterilization, or chemical gas sterilization. Resistance to chemical liquid and/or gas sterilization include, among others, resistance to sterilization with ethylene oxide gas, nitrogen dioxide gas, hydrogen peroxide gas plasma, peracetic acid immersion, ozone, glutaraldehyde and/or o-phthalaldehyde. The filter chosen is also inert or resistant to the fluid to which it will be used, for example pharmaceutical compositions containing drugs, such as antibiotics, anti-neoplastic agents, and antibodies.

In some embodiments, the medical connector further comprises a first cap or plug, for covering and protecting the distal opening and/or the connector at the distal end. The cap or plug is designed to prevent entry of dust and other contaminants into the first opening at the distal end, particularly during packaging and handling of the medical connector. In certain embodiments, the cap can be adapted to fit the type of connector at the distal end of the medical connector, e.g., snap cap, luer cap, friction fitting plug, etc.

For example, if the connector at the distal end is a luer lock connector, e.g., female luer lock, the cap is adapted to mate with the luer lock connector. In certain embodiments, a medical connector further comprises a second cap or plug, for covering and protecting the second opening at the proximal end. The first and/or second cap or plug is designed to fit tightly to the distal end and/or proximal end, but is easily removable when connecting the medical connector, e.g., a twistable lockable and twistable releasable mechanism. In certain embodiments of a cap, a plug is centrally located on the cap for occupying the space of the passageway, for example the space in the distal section of the passageway, when engaged onto the medical connector. In certain embodiments, when the cap with the plug is engaged on the medical connector, a space (i.e., gap) is present between the wall of the passageway and the exterior surface of the plug to provide for a loose-fit in the passageway, and have a space between the surface of the filter and the end of the plug.

The medical connector, including elements such as the body, the flange, fins and cap is made of any suitable material. In certain embodiments, the medical connector can be made of metal, such as surgical metal, or made of ceramic. In certain embodiments, the medical connector is made of plastic, including various thermoplastics, thermosets, elastomers and combinations thereof. Exemplary plastics include, among others, polyethylene, polypropylene, polyvinyl chloride, polystyrene, polyamide, polyester, and polyurethanes, polyetherether ketones, polysulfones, polyphenylene sulfide, polyisoprene, polybutadiene, polyurethane elastomers, and combinations thereof. In certain embodiments, the medical connector can be made of various polymer blends including among others, blends of polycarbonate-polyester, ABS and polycarbonate, polyethylene ether and polystyrene, polyvinyl chloride and ethylene vinyl acetate copolymer, polyvinyl chloride and ABS, and polyvinyl chloride and polyurethane. In preferred embodiments, the medical connector is made of plastic, particularly moldable plastic. In some embodiments, the plastic is chosen to provide sufficient resiliency and rigidity to resist the stresses and pressures placed on the medical connector, such as stresses imposed in connecting to other members (e.g., tubes, syringes, catheters, fluid reservoirs, luer connectors, etc.), forces imposed on the flange, and pressure of the fluids used with the medical connector. In various embodiments, the material used to make the medical connector is stable and/or inert to the substances to which it is meant to contact and/or be exposed, including therapeutic solutions, sterilization chemicals, ultraviolet light, and gamma radiation.

In view of the foregoing description, reference is made to the drawings, which describe various embodiments of the medical connector of the present disclosure. The embodiments presented in the drawings are considered exemplary and is not intended to limit the medical connector to the embodiments presented. Various other embodiments will be apparent to those skilled in the art and can be made in light of the guidance provided in the present disclosure.

Accordingly, referring to the drawings, FIGS. 1 to 6 show an exemplary embodiment of a medical connector in accordance with the present disclosure. In FIGS. 1 to 6, the medical connector 10 has a substantially cylindrical body, and has a distal end 11 and a proximal end 12. The distal end 11 defines a first opening 17 and includes a luer connector 23 for connection to another member (e.g., tube, syringe, fluid reservoir, catheter, luer connector, etc.). The proximal end 12 defines a second opening 15, which may be connected to another member, e.g., a tube. The body of the connector 10 defines a centrally located passageway extending along the longitudinal axis, which in FIGS. 1 and 3 to 6 are separated into a distal section 18 and an inner section 16, connecting the first opening 17 at the distal end and the second opening 15 at the proximal end. In FIGS. 1 and 3 to 6, the passageway also has a proximal section 13. The distal section 18 of the passageway is adapted or configured 23 to accept a male luer, particularly a male luer lock. The distal section 18 of the passageway can have a uniform bore (e.g., uniform diameter along the length of the passageway) or as shown in FIGS. 1 and 3 to 6 taper inward along its longitudinal axis towards the proximal end.

The inner section of the passageway 16 can have a uniform bore (e.g., diameter) along the longitudinal axis of the passageway, or as shown in FIGS. 1 and 3 to 6, have an outward taper along the longitudinal axis towards the proximal end of the passageway. The inner section of the passageway can be sufficiently tapered to reduce the resistance to the fluid flow along the longitudinal axis towards the proximal end 12. As shown in FIGS. 1 and 3 to 6, the passageway can also have a proximal section 13, with a different bore size than the inner section. While the proximal end 12 can be adapted to have a second connector, such as a luer connector or extended tube, in certain embodiments, the proximal section 13 of the passageway is dimensioned to accept another member, such as a tube. The tube can be inserted into the proximal section 13 of the passageway. To prevent accidental removal, tampering, or replacing of the tube at the proximal section of the passageway, the tube can be attached using an adhesive, such as a UV activated adhesive (e.g., DYMAX® 1120-M-UR UV Glue, DYMAX® 1120-M-T-UR UV Glue).

In FIGS. 1 and 3 to 6, the bore size of the distal section of the passageway is larger than the bore size of the inner section of the passageway, thus forming an annular surface 14 at the interface of the distal section and inner section of the passageway. While the annular surface can be a flat annular surface or a non-flat annular surface, in FIGS. 1 and 3 to 6 the annular surface is tapered inward towards the proximal end, such that the interface present between the distal section and inner section of the passageway is in the form of a frustrum (e.g., frustoconical) 14, where the narrow part of the frustrum connects to the inner section of the passageway. A flat annular surface 20 is present at the outer edge of the frustrum.

The filter 41 is disposed in the distal section of the passageway, at the interface between the distal section 18 and the inner section 16 of the passageway. A protruding annular ridge 19 in the distal section of the passageway keeps the filter 41 in place and prevents it from being dislodged. The protruding annular ridge can be continuous, being a continuous annular ridge, or in some embodiments, composed of separate protruding ridges, for example as protruding nubs or fingers, to hold the filter in place. The interface between the distal section and inner section of the passageway is in the form of a frustrum (e.g., frustoconical) 14, where the narrow part of the frustrum connects to the inner section of the passageway. This allows a fluid to move through substantially all of the surface area of the filter rather than being confined to the area defined by the cross-section of the inner section of the passageway. In various embodiments, the filter sits on a flat annular surface 20 at the outer edge of the frustrum, and seals tight against the wall of the distal section of the passageway 18. In various embodiments, securing the filter 41 to the wall of the passageway and/or the flat annular surface can be accomplished using an adhesive or by tight fitting or thermal fitting the filter into the passageway. In other embodiments, an annular ring (e.g., washer) can be positioned on top of the filter, where the annular ring holds the filter in place. In such embodiments, the filter is sandwiched between the annular ring on top of the filter and the flat annular surface at the outer edge of the frustrum. The filter can be any appropriate material and porosity, as discussed above. In certain embodiments, the filter has a porosity range from microporous to coarse, to filter out large particulates as well as microparticles.

As shown in FIGS. 1 to 6, the medical connector 10 has a proximal region 31, where the proximal region comprises one or more fins 32, each fin having a length along a longitudinal axis of the connector 10. The fins are provided to allow the user to hold the medical connector 10, and to turn the connector 10, e.g., when connecting or screwing the luer connector 23 at the distal end to another connector. In some embodiments, the body comprises two fins on opposite sides of the proximal region of the body. In other embodiments, the proximal region comprises three fins positioned equidistantly from each other around the proximal region of the body. In certain embodiments, the fins 32 are configured for holding with the fingers and protrude sufficiently outward from the body axis to generate torque when turning the connector, for example when connecting to another member, such as syringe or luer connector. In certain embodiments, as shown in FIGS. 7 to 10, the fins can have a recessed upper portion to provide comfortable surfaces to allow the user's fingers to engage the fins. The fins 32 are separate from the flange 21, described below, and spaced apart from the flange to form a space 22. In certain embodiments, the fins and flange are sufficiently spaced apart such that the space 22 accommodates fitting of a collar (e.g., a U-shaped open collar) for holding the medical connector.

The medical connector also comprises a flange 21, which in FIGS. 1 to 6 is a disc, protruding from the body between the distal end 11 or the connector at the distal end 23, and the proximal region 31 comprising the one or more fins 32. The flange, such as the disc, is dimensioned to form a shield and reduce the chances of the user from contacting the distal end 11, particularly the luer connector 23, when handling the medical connector 10. As discussed above, the flange can also act as a brace for holding the medical connector when a force is applied to it, such as when connected to a syringe and pressure is applied to the syringe plunger. As illustrated in FIG. 11, in certain embodiments, the size of the flange is dimensioned to brace against a collar, which collar can be closed or open, when a force is applied to the medical connector, for example, at the outlet of a syringe pump. In FIG. 11, the body of the medical connector 10 through the proximal region rests on an open collar 60 with the flange 21 braced against one side of the collar 60. The medical connector 10 is attached to the outlet of a syringe 61 and has a tubing 63 attached to the proximal end through the proximal section 13 of the passageway. When force is applied to the syringe plunger 62, the flange is forced against the collar 60 and fluid forced through the medical connector 10 and the tubing 63. The force on the syringe also keeps the medical connector 10 from coming off of the syringe 61. Thus, in certain embodiments, the flange is made sufficiently resilient and sufficiently rigid to withstand the forces applied on it in such applications.

As discussed above and as shown in FIGS. 1 to 4, in certain embodiments, the medical connector further comprises a first cap or plug 50 for covering the distal opening 17, thereby protecting it from contamination during packaging and handling. In certain embodiments, the cap is adapted to fit the connector 23 at the distal end 11. In a preferred embodiment, the cap is a luer cap 52, which connects to a luer connector 23. The cap can fit tightly on the connector 23, e.g., twistable lockable, but is easily removable, e.g., twistable releasable. In some embodiments, the cap has a centrally located plug 51, which is dimensioned to fill the space of the distal section of the passageway 18. Where the distal section of the passageway is a uniform bore, the corresponding centrally located plug 51 of the cap can be a uniform cylinder. Where the distal section of the passageway has an inwardly tapered bore along its length toward the proximal end, the corresponding centrally located plug of the cap can be a tapered cylinder, i.e., frustoconical. In typical embodiments, the plug on the cap is dimensioned to have a space (i.e., gap) between the wall of the passageway and the exterior surface of the plug to provide for a loose fit, and have a space between the surface of the filter and the end of the plug when the cap is engaged on the medical connector (see, e.g., FIG. 3). The exterior of the cap can have features for enhancing gripping of the cap, such as exterior ridges or grooves along the longitudinal axis, or bumps, dimples, and/or textured surfaces on the exterior surface of the cap.

An alternative embodiment of the medical connector in accordance with the present disclosure is shown in FIGS. 7 to 10. In FIGS. 7 to 10, the medical connector 10 has a distal end 11 and a proximal end 12. The distal end 11 defines a first opening 17 and includes a luer connector 23 for connection to another member (e.g., a tube, syringe, catheter, fluid reservoir, luer connector, etc.). The proximal end 12 defines a second opening 15, which may be connected to another member, e.g., a tube. The body also comprises a proximal region 31.

The medical connector 10 has a substantially cylindrical body, which has a centrally located passageway extending along the longitudinal axis and connecting the first opening 17 at the distal end 11 and the second opening 15 at the proximal end 12. The passageway is separated into different sections: a distal section 18 and an inner section 16. The passageway can further have a proximal section 13. The bore size (e.g., diameter) of the distal section 18 is larger than the bore size (e.g., diameter) of the inner section 16 of the passageway. The interface or transition of the distal section to the inner section of the passageway is a flat annular surface 24, with the opening in the ring forming the entry of the inner section 16 of the passageway and the exposed annular surface facing the distal end 11. In certain embodiments, a constriction 25 is present in the inner section of the passageway towards the distal end 11. In other embodiments, the constriction 25 is absent. The inner section 16 of the passageway can have a uniform bore (e.g., diameter) along the length of the passageway, or be tapered outward along the longitudinal axis towards the proximal end 12. An outwardly tapered inner section 16 of the passageway reduces resistance as fluid flows along the inner section 16 towards the proximal end 12. The proximal end 12 can have a second connector for connecting to another member; however as shown in FIGS. 7 to 10, the passageway has a proximal section 13, which is dimensioned to accept another member, such as a tube. The proximal section 13 as shown has a larger bore size than the inner section of the passageway. The other member, particularly a tube, can be attached to the proximal section. As discussed above, to prevent accidental removal, tampering, or replacing of the tube, an adhesive can be used to secure a tube to the proximal section 13 of the passageway.

The filter 41 is disposed or positioned in the distal section of the passageway, in-line with the fluid flow, at the interface between the distal section 18 and the inner section 16 of the passageway. In the embodiment shown in FIGS. 7 to 10, the filter 41 sits on the flat annular surface formed by the interface of the distal section and the inner section of the passageway. The filter can be secured by various ways, such as by tight fitting, thermal fitting, and/or an adhesive. In other embodiments, the filter can be held in place by a protruding annular ridge in the distal section, or sandwiched between another annular ring on top of the filter and the flat annular surface of the interface, as discussed above. In some embodiments, a foam, mesh, weave or like material supports the filter, with the foam, mesh or weave support resting on the flat annular surface of the interface. The filter 41 can be chosen according to the guidance provided herein.

The embodiment illustrated in FIGS. 7 to 10 includes a proximal region 31 comprising one or more fins 32, such as on opposing sides of the body, where each fin 32 has a length along the longitudinal axis of the medical connector 10 and has a recessed upper portion, which provides comfortable surfaces to allow the user's fingers to engage the fins. The flange, shown as a disc feature 21, protrudes from the connector body, between the distal end 11 or luer connector 23 and the proximal region comprising the one or more fins 32. The flange in the form of the disc acts as a shield to reduce the risk of the user from contacting the distal end 11 and the connector 23 when handling the medical connector 10 by the proximal region 31. In certain embodiments, the disc 21 is used to hold or brace the connector when force is applied to it during use, for example when attached to a syringe and force is applied to the syringe barrel. In some embodiments, the disc is dimensioned and sufficiently resilient and rigid to brace against a collar holding the connector, such as illustrated in FIG. 11. As noted above, the fins can be attached to the disc, or be separate or spaced apart 22 from the disc. In certain embodiments, the disc and the fins are sufficiently spaced apart to provide for insertion into a collar, such as a U-shaped collar for holding the medical connector 10.

In some embodiments (not shown), an additional filter is arranged between the passageway 16 and the opening 15 at the proximal end 12 of the medical connector embodiments described above. In some embodiments (not shown), one or more additional filters may be arranged between the opening 15 at the proximal end 12 and the opening 17 at the distal end 11. The additional filters may be the same as filter 41, or may include one or more different filters, e.g., different membranes and/or materials.

In another aspect, the medical connector is part of an infusion system. Accordingly, in some embodiments, an infusion system comprises a medical connector of the present disclosure. In certain embodiments of the infusion system, a tubing, particularly a flexible tubing, is attached to the proximal end of the medical connector, e.g., through the proximal section of the passageway. In certain embodiments of the infusion system, an injection needle, e.g., for subcutaneous or intravenous administration, is attached to the tubing at the end not attached to the proximal end of the medical connector. In other embodiments, the infusion system comprising the medical connector further comprises a constant force pump, particularly a constant force syringe spring pump (e.g., Freedom60® pump: RMS Medical Systems, New York).

In a further aspect, the medical connector is provided in the form of a kit. In some embodiments, the kit comprises a medical connector of the present disclosure. In certain embodiments, the kit further comprises a tubing set. In certain embodiments, a tubing, particularly a flexible tubing, is attached to the proximal end of the medical connector, e.g., at the proximal section of the passageway. In certain embodiments, the kit also comprises an injection needle set, such as for subcutaneous or intravenous administration. The needle can be separate or where the kit further comprises a tubing, an injection needle can be attached to the end of the tubing not connected to the medical connector, or the tubing can have a connector at the end not connected to the medical connector to connect to different injection needles of the injection needle set.

In some embodiments, the kit comprises a medical connector of the disclosure, and a pump, particularly a constant force spring pump, more particularly a constant force syringe spring pump (e.g., Freedom60® pump). In certain embodiments, the kit comprising the medical connector and pump, further comprises a tubing, where the tubing is attached to the medical connector. In certain embodiments, the kit further comprises an injection needle set, such as for intravenous or subcutaneous administration. Where the kit includes a tubing and an injection needle set, an injection needle can be attached to the tubing at the end not connected to the medical connector, or the tubing can have a connector at the end not connected to the medical connector to connect to different injection needles of the needle set.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A medical connector for liquid infusion systems comprising:
   a unitary body defining a first opening at a distal end, a second opening at a proximal end, and a central passageway comprising a distal section and an inner section connecting the first and second openings;
   a connector at the distal end;
   a proximal region towards the proximal end of the unitary body;
   a radial flange protruding from the unitary body between the proximal region and the connector at the distal end, the radial flange structured and arranged to shield the connector from an operator's fingers, and brace the connector when force is applied by an infusion system; and
   an in-line filter positioned in the distal section of the passageway and seated upon an annular surface at an interface between the distal section and the inner section between the first opening at the distal end and the second opening at the proximal end.

2. The medical connector according to claim 1, wherein the unitary body comprises a substantially cylindrical unitary body.

3. The medical connector according to claim 1, wherein the proximal region comprises one or more fins.

4. The medical connector according to claim 1, wherein the one or more fins have a recessed upper portion.

5. The medical connector according to claim 1, wherein the connector at the distal end of the unitary body is a luer connector.

6. The medical connector according to claim 5, wherein the luer is a luer lock.

7. The medical connector according to claim 1, wherein the radial flange comprises a disc.

8. The medical connector according to claim 1, wherein the distal section of the passageway has a larger bore size than the bore size of the inner section of the passageway, thereby forming an interface between the distal section and inner section of the passageway.

9. The medical connector according to claim 1, wherein the passageway is formed by a single piece of material.

10. The medical connector according to claim 1, wherein the filter comprises a microporous membrane.

11. The medical connector according to claim 10, wherein the microporous membrane is selected from the group consisting of acrylic co-polymer membrane, cellulose acetate membrane, nitrocellulose membrane, nylon membrane, polyethersulfone (PES) membrane, polypropylene membrane, polysulfone membrane, polytetrafluoroethylene (PTFE) membrane, and polyvinylidene fluoride (PVDF) membrane.

12. The medical connector according to claim 1, wherein the filter comprises an asymmetric membrane.

13. The medical connector according to claim 12, wherein the asymmetric membrane is selected from the group consisting of polyethersulfone (PES) membrane, polysulfone membrane, polyvinylidene fluoride (PVDF) membrane, and combinations thereof.

14. The medical connector according to claim 1, wherein the filter comprises an ultrafiltration membrane.

15. The medical connector according to claim 14, wherein the ultrafiltration membrane is selected from the group consisting of polysulfone membrane, polypropylene membrane, cellulose acetate membrane, and regenerated cellulose membrane.

16. The medical connector according to claim 1, wherein the filter comprises a coarse filter.

17. The medical connector according to claim 16, wherein the coarse filter is selected from the group consisting of glass fiber filter, metal screen filter, polyester filter, and polypropylene filter.

18. The medical connector according to claim 1, further comprising at least one additional filter interposed in the passageway between the first and second openings.

19. The medical connector according to claim 1, wherein the passageway further comprises a proximal section, wherein the proximal section is connected to a tubing.

20. The medical connector according to claim 19, further comprising an injection needle attached to the tubing at the end not connected to the proximal section.

21. The medical connector according to claim 1, wherein the proximal end is adapted for a second connector.

22. The medical connector according to claim 21, wherein the second connector comprises a second luer.

23. The medical connector according to claim 1, further comprising a cap or plug for covering the first opening at the distal end.

24. The medical connector according to claim 23, wherein the cap or plug is adapted for a luer connector.

25. The medical connector according to claim 24, wherein the cap is adapted for a luer lock.

26. A connector for liquid infusion systems comprising:
a substantially cylindrical unitary body defining a first opening at a distal end, a second opening at a proximal end, and a passageway comprising a distal section and an inner section connecting the first and second openings;
a luer connector at the distal end;
one or more fins protruding from the unitary body;
a disc protruding from the unitary body between the one or more fins and the luer connector, the disc structured and arranged to shield the connector from an operator's fingers, and brace the connector when force is applied by an infusion system; and
an in-line filter positioned in the distal section of the passageway and seated upon an annular surface at an interface between the distal section and the inner section between the first opening and the second opening.

27. The connector according to claim 26, wherein the one or more fins have a recessed upper portion.

28. The connector according to claim 26, wherein the luer connector is a luer lock.

29. The connector according to claim 26, wherein the distal section of the passageway has a larger bore size than the bore size of the inner section of the passageway, thereby forming an interface between the distal section and inner section of the passageway.

30. The connector according to claim 26, wherein the passageway of is formed by a single piece of material.

31. The connector according to claim 26, wherein the filter comprises a microporous membrane.

32. The connector according to claim 31, wherein the microporous membrane is selected from the group consisting of acrylic co-polymer membrane, cellulose acetate membrane, nitrocellulose membrane, nylon membrane, polyethersulfone (PES) membrane, polypropylene membrane, polysulfone membrane, polytetrafluoroethylene (PTFE) membrane, and polyvinylidene fluoride (PVDF) membrane.

33. The connector according to claim 26, wherein the filter comprises an asymmetric membrane.

34. The connector according to claim 33, wherein the asymmetric membrane is selected from the group consisting of polyethersulfone (PES) membrane, polysulfone membrane, polyvinylidene fluoride (PVDF) membrane, and combinations thereof.

35. The connector according to claim 26, wherein the filter comprises an ultrafiltration membrane.

36. The connector according to claim 35, wherein the ultrafiltration membrane is selected from the group consisting of polysulfone membrane, polypropylene membrane, cellulose acetate membrane, and regenerated cellulose membrane.

37. The connector according to claim 26, wherein the filter comprises a coarse filter.

38. The connector according to claim 37, wherein the coarse filter is selected from the group consisting of glass fiber filter, metal screen filter, polyester filter, and polypropylene filter.

39. The connector according to claim 26, further comprising at least one additional filter interposed in the passageway between the first and second openings.

40. The connector according to claim 26, wherein the passageway further comprises a proximal section, wherein the proximal section is connected to a tubing.

41. The connector according to claim 40, further comprising an injection needle attached to the tubing at the end not connected to the proximal section.

42. The connector according to claim 26, wherein the proximal end is adapted for a second connector.

43. The connector according to claim 42, wherein the second connector comprises a second luer.

44. The connector according to claim 26, further comprising a cap or plug for covering the first opening at the distal end.

45. The connector according to claim 44, wherein the cap or plug is adapted for a luer connector.

46. The connector according to claim 45, wherein the cap is adapted for a luer lock.

47. A kit for liquid infusion comprising:
   a connector, including:
      a substantially cylindrical unitary body defining a first opening at a distal end, a second opening at a proximal end, and a passageway comprising a distal section and an inner section connecting the first and second openings;
      a luer connector at the distal end;
      one or more fins protruding from the unitary body;
      a disc protruding from the unitary body between the one or more fins and the luer connector, the disc structured and arranged to shield the connector from an operator's fingers, and brace the connector when force is applied by an infusion system; and
      an in-line filter positioned in the distal section of the passageway and seated upon an annular surface at an interface between the distal section and the inner section between the first opening and the second opening;
   a tubing set attached to the proximal end of the connector;
   a pump.

48. The kit according to claim 47, wherein the pump is a constant force pump.

49. The kit according to claim 48, wherein the constant force pump is a constant force syringe spring pump.

50. The kit according to claim 47, further including at least one injection needle.

* * * * *